United States Patent
Pierce et al.

(10) Patent No.: US 10,426,847 B2
(45) Date of Patent: Oct. 1, 2019

(54) METHOD FOR THE TREATMENT OF MALIGNANCIES

(71) Applicants: OncoSec Medical Incorporated, San Diego, CA (US); Robert H. Pierce, Seattle, WA (US); Adil Daud, Hillsborough, CA (US)

(72) Inventors: Robert H. Pierce, Seattle, WA (US); Adil Daud, Hillsborough, CA (US)

(73) Assignee: OncoSec Medical Incorporated, San Diego, CA (US)

( * ) Notice: Subject to any disclaimer, the term of this patent is extended or adjusted under 35 U.S.C. 154(b) by 0 days.

(21) Appl. No.: 15/561,915

(22) PCT Filed: Mar. 24, 2016

(86) PCT No.: PCT/US2016/024079
§ 371 (c)(1),
(2) Date: Sep. 26, 2017

(87) PCT Pub. No.: WO2016/154473
PCT Pub. Date: Sep. 29, 2016

(65) Prior Publication Data
US 2018/0318393 A1 Nov. 8, 2018

Related U.S. Application Data

(60) Provisional application No. 62/309,131, filed on Mar. 16, 2016, provisional application No. 62/138,793, filed on Mar. 26, 2015.

(51) Int. Cl.
| | | |
|---|---|---|
| *A61K 48/00* | (2006.01) | |
| *A61K 38/19* | (2006.01) | |
| *A61K 38/20* | (2006.01) | |
| *A61K 39/395* | (2006.01) | |
| *C07K 16/28* | (2006.01) | |
| *A61N 1/32* | (2006.01) | |
| *C07K 14/54* | (2006.01) | |
| *A61N 1/36* | (2006.01) | |

(52) U.S. Cl.
CPC .......... *A61K 48/0091* (2013.01); *A61K 38/19* (2013.01); *A61K 38/208* (2013.01); *A61K 39/3955* (2013.01); *A61N 1/327* (2013.01); *C07K 14/5434* (2013.01); *C07K 16/2818* (2013.01); *A61N 1/36002* (2017.08); *C07K 2317/569* (2013.01); *C07K 2317/73* (2013.01); *C07K 2317/76* (2013.01); *C12N 2800/22* (2013.01)

(58) Field of Classification Search
CPC .................. A61K 48/00091; A61K 38/102
See application file for complete search history.

(56) References Cited

U.S. PATENT DOCUMENTS

| 8,026,223 B1 | 9/2011 | Heller et al. |
| 8,802,643 B1 | 8/2014 | Heller et al. |
| 2015/0017121 A1 | 1/2015 | Becher et al. |

FOREIGN PATENT DOCUMENTS

WO  WO 2006/121168 A1  11/2016

OTHER PUBLICATIONS

Daud et al. (2008) J. Clin. Oncol. 26(36):5896-5903 "Phase I trial of interleukin-12 plasmid electroporation in patients with metastatic melanoma".
Nirschl and Drake (2013) Clin Cancer Res. 19(18):4917-4924 "Molecular pathways: coexpression of immune checkpoint molecules: signaling pathways and implications for cancer immunotherapy".
Tumeh et al. (2014) Nature 515(7528):568-571 "PD-1 blockade induces responses by inhibiting adaptive immune resistance".
International Search Report and Written Opinion for Application No. PCT/US2016/024079 dated Jun. 24, 2016 (9 pages).
Bonehill et al., (2009) Clin. Cancer Res. 15(10):3366-3375 "Single-step antigen loading and activation of dendritic cells by mRNA electroporation for the purpose of therapeutic vaccination in melanoma patients".
Lee, W.G., et al., "Microscale electroporation: challenges and perspectives for clinical applications," Integrative Biology, 1(3): 242-251 (2009).
Extended European Search Report for corresponding European Application No. 16769720.0, dated Oct. 18, 2018, 12 pages.
Daud et al: Intratumoral Electroporation of Plasmid Interleukin-12: Efficacy and Biomarker Analyses From a Phase 2 Study in Melanoma (OMS-I100), Journal of Translational Medicine, Biomed Central, vol. 13 (Suppl 1), Jan. 15, 2015, 2 pages.
Lee et al: Inhibition of Established Subcutaneous and Metastatic Murine Tumors by Intramuscular Electroporation of the Interleukin-12 Gene; Journal of Biomedical Science, XP002982809, 14 pages.
Agarwala: Intralesional Treatment for Advanced Melanoma: What's on the horizon, XP002785129, Elsevier Science Publishers, Amsterdam, NL, 1 page.

(Continued)

*Primary Examiner* — Marcia S Noble
(74) *Attorney, Agent, or Firm* — Alston & Bird LLP

(57) ABSTRACT

The present invention provides for the intratumoral delivery of at least one immunostimulatory cytokine in combination with at least one checkpoint inhibitor. In particular, it provides delivery of a plasmid encoding the immunostimulatory cytokine using intratumoral electroporation. The checkpoint inhibitor may be administered systemically or encoded on a plasmid and delivered using intratumoral electroporation. The checkpoint inhibitor may be delivered contemporaneously with or after treatment with the immunomodulatory cytokine.

18 Claims, 4 Drawing Sheets

(56) References Cited

OTHER PUBLICATIONS

Bhatia et al: Intratumoral Deliver of Interleukin-12 DNA via in Vivo Electroporation Leads to Regression of Injected and Non-Injected Tumors in Merkel Cell Carcinoma: Final Results of a Phase 2 Study, European Journal of Cancer, Elsevier, Amsterdam, NL, 1 page.

METHOD FOR THE TREATMENT OF MALIGNANCIES

This filing is a 371 US National Phase filing of PCT Patent Application No. PCT/US2016/024079, filed Mar. 24, 2016, which claims benefit from Provisional Patent Application Nos. 62/309,131 filed Mar. 16, 2016 and 62/138,793 filed Mar. 26, 2015, each of which is incorporated herein by reference.

FIELD OF THE INVENTION

The present invention provides for the intratumoral delivery of immune checkpoint inhibitors. In particular, it provides delivery of checkpoint inhibitors by intratumoral electroporation.

BACKGROUND OF THE INVENTION

Immunotherapy has recently drawn attention as a fourth method following surgery, chemotherapy and radiation therapy for treating tumors. Since immunotherapy utilizes the immunity inherent to humans, it is said that the physical burden on patients are less in immunotherapy than those in other therapies. The therapeutic approaches known as immunotherapies include: cell transfer therapy in which cells such as lymphokine-activated cells, natural killer T-cells or γδT cells obtained, for example, from exogenously-induced cytotoxic T-lymphocytes (CTLs) or peripheral blood lymphocytes by expansion culture using various method are transferred; dendritic cell-transfer therapy or peptide vaccine therapy by which in vivo induction of antigen-specific CTLs is expected; Th1 cell therapy; and immune gene therapy in which genes expected to have various effects are introduced ex vivo into the above-mentioned cells to transfer them in vivo. In these immunotherapies, CD4-positive T cells and CD8-positive T cells have traditionally been known to play a critical role.

In humans with cancer, antitumor immunity is often ineffective due to the tight regulation associated with the maintenance of immune homeostasis. One of the major limitations is a process known as 'T-cell exhaustion', which results from chronic exposure to antigens and is characterized by the upregulation of inhibitory receptors. These inhibitory receptors serve as immune checkpoints in order to prevent uncontrolled immune reactions. Blocking of one or several of these immune checkpoints with monoclonal antibodies (mAbs) has been shown to rescue otherwise exhausted antitumor T cells, and most importantly, has been associated with objective clinical responses in cancer patients.

Optimal T cell activation requires contemporaneous signals through the T cell receptor and costimulatory molecules. CD28, the prototypical costimulatory molecule, upon interaction with its ligands B7-1 and B7-2, plays a crucial role in initial T cell priming (see, e.g., Sharpe et al., (2002) *Nat. Rev. Immunol.* 2:203-209). CD28-mediated T cell expansion is opposed by another B7-1,2 counter receptor, cytotoxic T lymphocyte associated antigen 4 (CTLA-4), which attenuates the proliferation of recently activated T cells (see, e.g., Krummel et al., (1996) *J. Exp. Med.* 183: 2533-2540; Leach et al., (1996) *Science* 271:1734-1736).

The identification and characterization of additional CD28 and B7 family members PD-1 (programmed death-1), PD-L1 (programmed death ligand-1 or B7-H1), and PD-L2 (B7-DC) has added further complexity to the process of T-cell activation and peripheral tolerance in humans. Similar to the B7-1 and B7-2/CTLA-4 interaction, PD-1 interactions with PD-L1 and PD-L2 downregulate central and peripheral immune responses (see, e.g., Fife et al., (2008) *Immunol. Rev.* 224:166-82). Accordingly, antibody-based blockade of PD-1, like CTLA-4, is also being explored in human clinical trials for the treatment of cancer (see, e.g., Berger et al. (2008) *Clin. Cancer Res.* 14:3044-3051). Nevertheless, as with CTLA-4, improved therapies are still needed.

In vivo electroporation is a gene delivery technique that has been used successfully for efficient delivery of plasmid DNA to many different tissues. Studies have reported the administration of in vivo electroporation for delivery of plasmid DNA to B16 melanomas and other tumor tissues. Systemic and local expression of a gene or cDNA encoded by a plasmid can be obtained with administration of in vivo electroporation. Use of in vivo electroporation enhances plasmid DNA uptake in tumor tissue, resulting in expression within the tumor, and delivers plasmids to muscle tissue, resulting in systemic expression of certain immunomodulatory molecules, such as cytokines.

It has been shown that electroporation can be used to transfect cells in vivo with plasmid DNA. Recent studies have shown that electroporation is capable of enhancing delivery of plasmid DNA as an antitumor agent. Electroporation has been administered for treatment of hepatocellular carcinomas, adenocarcinoma, breast tumors, squamous cell carcinoma and B16.F10 melanoma in rodent models. The B16.F10 murine melanoma model has been used extensively for testing potential immunotherapy protocols for the delivery of an immunostimulatory molecule including cytokines either as recombinant protein or by gene therapy.

Various protocols known in the art can be utilized for the delivery of plasmid encoding a checkpoint inhibitor utilizing in viva electroporation for the treatment of cancer. The protocols known in the art describe in vivo electroporation mediated cytokine based gene therapy, both intratumor and intramuscular, utilizing low-voltage and long-pulse currents.

Accordingly, what is needed in the art is a combination therapy of intratumoral immunostimulatory cytokine therapy and a checkpoint inhibitor, co-delivered encoded on a plasmid and delivered via electroporation to the tumor; or via systemic delivery of the checkpoint inhibitor protein therapeutic, either concurrently with or subsequent to, the intratumoral immunostimulatory cytokine therapy, that will provide substantially improved results in the regression of cancer tumors, such as melanoma, while also substantially improving the long-term survival rates.

SUMMARY OF THE INVENTION

Figure 1:
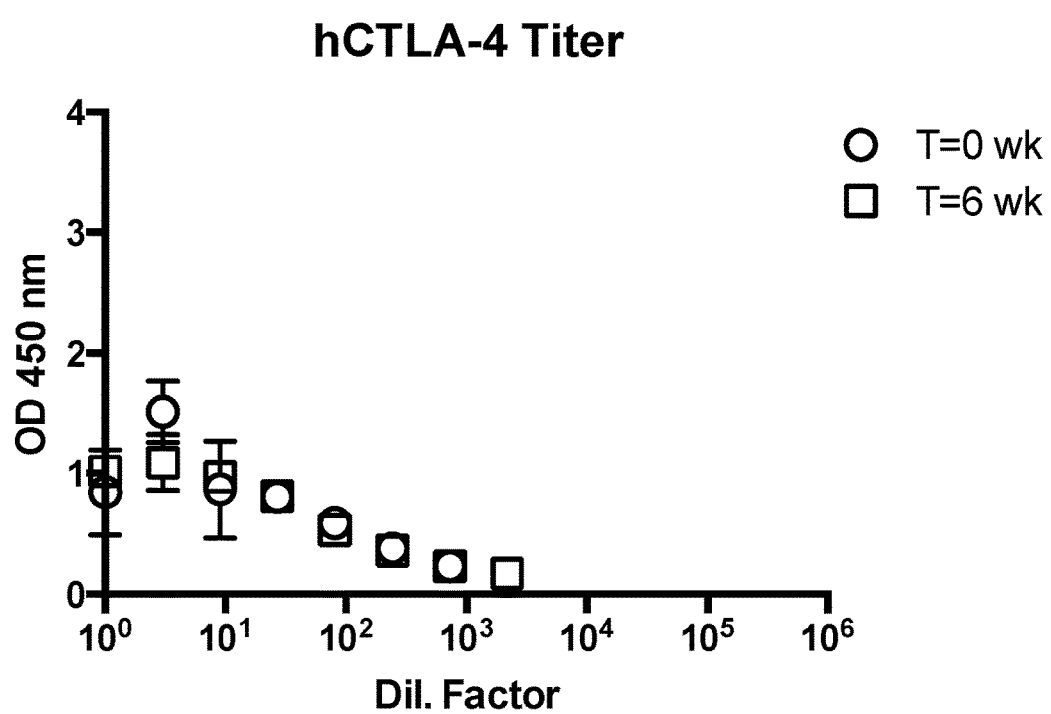
FIG. 1 shows the titer of anti-hCTLA-4 antibodies 6 weeks post immunization of a llama.
Figure 2:
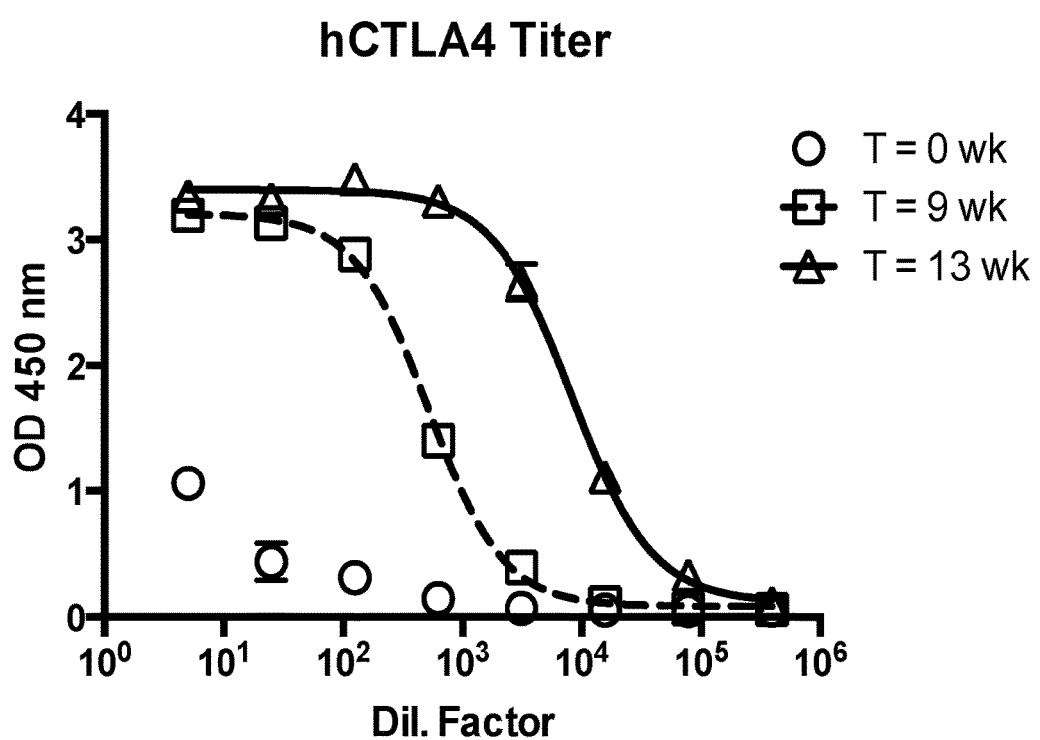
FIG. 2 shows the titer of anti-hCTLA-4 antibodies at weeks 0, 9, and 13 post immunization. The titer at week 9 was measured one week after the llama was given a 50 μg hCTLA4 protein boost. The titer at week 13 was measured two weeks after two 500 μg hCTLA-4 protein boosts.

The present invention provides a method of treating a subject having a cancerous tumor, the method comprising:

a) injecting the cancerous tumor with an effective dose of at least one plasmid coding for at least one immunostimulatory cytokine(s);

b) administering electroporation therapy to the tumor; and c) administering an effective dose of a checkpoint inhibitor to the subject. In a certain embodiment, the electroporation therapy comprises the administration of at least one voltage pulse over a duration of about 100 microseconds to about 1 millisecond. The voltage pulse can be delivered to the tumor is from about 200 V/cm to about 1500 V/cm. In another embodiment, the checkpoint inhibitor is administered systemically. In another embodiment, the checkpoint inhibitor is encoded on a plasmid and delivered to the cancerous tumor by electroporation therapy. In another embodiment, the checkpoint inhibitor(s) is encoded on the plasmid encoding the immunostimulatory cytokine and delivered to the cancerous tumor by electroporation therapy. The checkpoint inhibitor is an antagonist of at least one checkpoint target of Table 1. In a further embodiment, the method of claim 7, wherein the checkpoint inhibitor is selected from the group consisting of: nivolumab (ONO-4538/BMS-936558, MDX1106, OPDIVO), pembrolizumab (MK-3475, KEYTRUDA), pidilizumab (CT-011), and MPDL328OA (ROCHE). In yet a further embodiment, checkpoint inhibitor is administered after electroporation of the immunostimulatory cytokine. The plasmid coding for an immunostimulatory cytokine is selected from Table 2. In a certain embodiment, the immunostimulatory cytokine is IL-12.

The cancerous tumor is melanoma.

The present invention encompasses, a method of treating a subject having a cancerous tumor, the method comprising:

a) administering a first electroporation therapy at time T1, wherein the first treatment further comprises injecting the cancerous tumor with a first effective dose of plasmid coding for a immunostimulatory cytokine(s);

b) administering a first electroporation therapy to the tumor at time T1, the first electroporation therapy further comprising the administration of at least one voltage pulse having a duration of about 100 microseconds to about 20 milliseconds;

c) administering a second treatment at time T2, wherein time T2 is a time later than time T1, wherein the second treatment further comprises injecting the cancerous tumor with a second effective dose of at least one plasmid coding for at least one immunostimulatory cytokine;

d) administering a second electroporation therapy to the tumor at time T2, the second electroporation therapy further comprising the administration of at least one voltage pulse having a duration of about 100 microseconds to about 20 milliseconds;

e) administering a third treatment at time T3, wherein time T3 is a time later than time T2, wherein the third treatment further comprises injecting the cancerous tumor with a third effective dose of plasmid coding for a therapeutic protein;

f) administering a third electroporation therapy to the tumor, the third electroporation therapy further comprising the administration of at least one voltage pulse having a duration of about 100 microseconds to about 20 milliseconds; and g) administering a checkpoint inhibitor after time T3. In another embodiment, the one voltage pulse delivered to the tumor has a field strength of about 200 V/cm to about 1500 V/cm. In a further embodiment, the checkpoint inhibitor is an antagonist of at least one checkpoint target of Table 1. The checkpoint inhibitor is selected from the group consisting of: nivolumab (ONO-4538/BMS-936558, MDX1106, OPDIVO), pembrolizumab (MK-3475, KEYTRUDA), pidilizumab (CT-011), and MPDL328OA (ROCHE), and the checkpoint inhibitor is delivered systemically. In another embodiment, the checkpoint inhibitor is encoded on a plasmid and delivered to the cancerous tumor by electroporation therapy. In certain embodiments, the checkpoint inhibitor is administered after electroporation of the immunostimulatory cytokine, and the plasmid coding for an immunostimulatory cytokine is selected from Table 2. In a further embodiment, the immunostimulatory cytokine is IL-12.

The cancerous tumor is melanoma.

A treatment schedule for a patient suffering from a cancerous tumor, wherein the treatment schedule comprises:

a) at least one cycle of intratumoral delivery of a plasmid encoding an immunostimulatory cytokine by electroporation;

b) an interval of at least 20-120 days following the one cycle;

c) administration to the patient, of a checkpoint inhibitor or a combination of the checkpoint inhibitor with an at least one additional cycle of intratumoral delivery of a plasmid encoding an immunostimulatory cytokine by electroporation. In a further embodiment, the checkpoint inhibitor is an anti-PD-1 or anti-PD-L1 therapy. In particular, the anti-PD-1/anti PD-L1 therapy is selected from the group consisting of: nivolumab (ONO-4538/BMS-936558, MDX1106, OPDIVO), pembrolizumab (MK-3475, KEYTRUDA), pidilizumab (CT-011), and MPDL328OA (ROCHE). In one embodiment, the cycle of intratumoral delivery comprises at least one electric pulse having a field strength of about 20 V/cm to about 1500 V/cm, and a duration of about 100 microseconds to about 20 milliseconds. In a further embodiment, the cycle comprises three treatments on day 1, day 5 and day 8. In yet another embodiment, the patient is treated with at least 3 cycles.

DETAILED DESCRIPTION OF THE INVENTION

As used herein, including the appended claims, the singular forms of words such as "a," "an," and "the," include their corresponding plural references unless the context clearly dictates otherwise.

All references cited herein are incorporated by reference to the same extent as if each individual publication, patent application, or patent, was specifically and individually indicated to be incorporated by reference.

Definitions

As used herein, "immune checkpoint" molecules refers to a group of immune cell surface receptor/ligands which induce T cell dysfunction or apoptosis. These immune inhibitory targets attenuate excessive immune reactions and ensure self-tolerance. Tumor cells harness the suppressive effects of these checkpoint molecules. Immune checkpoint target molecules include, but are not limited to, the checkpoint targets described in Table 1.

TABLE 1

Checkpoint Targets Accession Numbers

| Target | Unabbreviated Name | GenBank Accession Number - Mouse Nucleic Acid | GenBank Accession Number - Mouse Amino Acid | GenBank Accession Number - Human Nucleic Acid | GenBank Accession Number - Human Amino Acid |
|---|---|---|---|---|---|
| CTLA-4 | Cytotoxic T Lymphocyte Antigen-4 | U90271 | AAD00697 | L15006 | AAL07473 |
| PD-1 | Programmed Death 1 | NM_008798.2 | MP_032824 | NM_005018 | NP_005009.2 |
| PD-L1 | Programmed Death Ligand 1 | GQ904197 | ADK70950 | AY254342 | AAP13470 |
| LAG-3 | Lymphocyte Activation Gene-3 | AY230414 | AAP57397 | X51985 | CAA36243 |
| TIM3 | T cell Immunoglobulin Mucin-3 | AF450241 | AAL35776 | JX049979 | AFO66593 |
| KIR | Killer Cell Imunoglobulin-like Receptor | AY130461 | AY130461.1 | AY601812 | AAT11793 |
| BTLA | B- and T-Lymphocyte Attenuator | AY293285 | AAP44002 | AY293286 | AAP44003 |
| A2aR | Adenosine A2a Receptor | NM_009630 | NP_033760 | NP_001265428 | NM_001278499 |
| HVEM | Herpes Virus Entry Mediator | AF515707 | AAQ08183 | AY358879 | AAQ89238 |

The phrase "immune checkpoint inhibitor" includes molecules that prevent immune suppression by blocking the effects of immune checkpoint molecules. Checkpoint inhibitors can include antibodies and antibody fragments, nanobodies, diabodies, soluble binding partners of checkpoint molecules, small molecule therapeutics, peptide antagonists, etc. Inhibitors include, but are not limited to, to the checkpoint inhibitors described in Table 1.

The phrase "immunostimulatory cytokine" includes cytokines that mediate or enhance the immune response to a foreign antigen, including viral, bacterial, or tumor antigens. Innate immunostimulatory cytokines can include, e.g., TNF-α, IL-1, IL-10, IL-12, IL-15, type I interferons (IFN-α and IFN-β), IFN-γ, and chemokines. Adaptive immunostimulatory cytokines include, e.g., IL-2, IL-4, IL-5, TGF-β, IL-10 and IFN-γ. Examples of immunostimulatory cytokines are provided in Table 2 below.

The term "cancer" includes a myriad of diseases generally characterized by inappropriate cellular proliferation, abnormal or excessive cellular proliferation. Examples of cancer include but are not limited to, breast cancer, colon cancer, prostate cancer, pancreatic cancer, melanoma, lung cancer, ovarian cancer, kidney cancer, brain cancer, or sarcomas. Such cancers may be caused by, environmental factors, chromosomal abnormalities, degenerative growth and developmental disorders, mitogenic agents, ultraviolet radiation (UV), viral infections, inappropriate tissue expression of a gene, alterations in expression of a gene, or carcinogenic agents.

The term "treatment" includes, but is not limited to, inhibition or reduction of proliferation of cancer cells, destruction of cancer cells, prevention of proliferation of cancer cells or prevention of initiation of malignant cells or

TABLE 2

Immunostimulatory Cytokines Accession Numbers

| Cytokine | GenBank Accession Number - Mouse Nucleic Acid | GenBank Accession Number - Mouse Amino Acid | GenBank Accession Number - Human Nucleic Acid | GenBank Accession Number - Human Amino Acid |
|---|---|---|---|---|
| TNFα | M20155 | CAA68530 | X02910 | ADV31546 |
| IL-1 | RNU48592 | CAA28637 | X03833 | CAA27448 |
| IL-10 | MUSIL10Z | AAA39275 | HSU16720 | AAA80104 |
| IL-12 | NM_001159424.2 | NP_001152896.1 | NM_000882.3 | AAD16432 |
| p35 | NM_001303244.1 | NP_001290173.1 | NM_002187.2 | NP_000873.2 |
| p40 | | | | NP_002178.2 |
| IL-15 | NM_001254747.1 | NP_001241676 | NM_000585.4 | NP_000576 |
| IL-15Rα | NM_008358.2 | NP_032384 | NM_002189.3 | NP_002180 |
| IFNα | NM_010502.2 | NP_034632.2. | NM_006900.3. | NP_008831.3 |
| | | | NM_024013.2. | NP_076918.1 |
| IFNβ | NM_010510.1 | NP_034640.1 | NM_002176.3. | NP_002167.1. |
| IFNγ | NM_008337.4. | NP_032363.1. | NM_000619.2. | NP_000610.2 |
| IL-2 | NM_008366.3. | NP_032392.1. | NM_000586.3. | NP_000577.2. |
| TGFβ | NM_011577.2. | NP_035707.1 | NM_000660.5. | NP_000651.3. | arrest or reversal of the progression of transformed premalignant cells to malignant disease or amelioration of the disease.

The term "subject" refers to any animal, preferably a mammal such as a human. Veterinary uses are also intended to be encompassed by this invention.

The terms "electroporation", "electro-permeabilization," or "electro-kinetic enhancement" ("EP") as used interchangeably herein refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

The term "biomolecule" as used herein, encompasses plasmid encoded antibodies, antibody fragments, full length immunomodulatory proteins, soluble domains of membrane anchored molecules, fusion proteins, and the like.

Antibodies

The present invention provides an immunotherapeutic approach for reducing the size of a tumor or inhibiting the growth of cancer cells in an individual, or reducing or inhibiting the development of metastatic cancer in an individual suffering from cancer. Therapy is achieved by either systemic delivery of protein therapeutics, or intratumoral delivery of plasmids encoding various soluble forms of checkpoint inhibitors, using electroporation. Checkpoint inhibitor therapy may occur before, during, or after intratumoral delivery by electroporation of an immunostimulatory cytokine, e.g., IL-12.

Checkpoint inhibitors may be in the form of antibodies or antibody fragments, both of which can be encoded in a plasmid and delivered to the tumor by electroporation, or delivered as proteins/peptides systemically. As noted above, delivery of the checkpoint inhibitor therapeutic can occur before, during or after intratumoral delivery by electroporation of an immunostimulatory cytokine, e.g., IL-12.

The term "antibody" as used herein includes immunoglobulins, which are the product of B cells and variants thereof. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass.

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains, respectively.

Antibodies exist as full length intact antibodies or as a number of well-characterized fragments produced by digestion with various peptidases or chemicals. Thus, for example, pepsin digests an antibody below the disulfide linkages in the hinge region to produce F(ab')2, a dimer of Fab which itself is a light chain joined to VH-$CH_1$ by a disulfide bond. The F(ab')2 may be reduced under mild conditions to break the disulfide linkage in the hinge region thereby converting the F(ab')2 dimer into an Fab' monomer. The Fab' monomer is essentially a Fab fragment with the hinge region (see, Fundamental Immunology, W. E. Paul, ed., Raven Press, N.Y. (1993), for a more detailed description of other antibody fragments). A Fab fragment and Fc fragment are generated by digesting IgG with papain. Papain cleaves in the hinge region just above the residues involved in interchain S—S bonding, resulting in monovalent Fab fragments and the Fc fragment, which includes two constant region fragments, each containing the lower part of the hinge, CH2 and CH3 domains. The constant region fragments of the Fc are stabilized as a dimer though interchain S—S bonding of the lower residues of the hinge region.

Immunoglobulin "Fc" classically refers to the portion of the constant region generated by digestion with papain. Includes the lower hinge which has the interchain S—S bonds. The term "Fc" as used herein refers to a dimeric protein comprising a pair of immunoglobulin constant region polypeptides, each containing the lower part of the hinge, CH2 and CH3 domain. Such "Fc" fragment may or may not contain S—S interchain bridging in the hinge region. It should be understood that an Fc may be from any Ig class and, as such, may include a CH4 domain such as in the case of IgM. Mutant sequences of an Fc are known such as described by Wines et al., J. Immunol. 2000 May 15; 164(10):5313-8 and may be used herein.

While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

Recombinant antibodies may be conventional full length antibodies, antibody fragments known from proteolytic digestion, unique antibody fragments such as Fv or single chain Fv (scFv), domain deleted antibodies, and the like. Fragments may include domains or polypeptides with as little as one or a few amino acid deleted or mutated while more extensive deletion is possible such as deletion of one or more domains.

An Fv antibody is about 50 Kd in size and comprises the variable regions of the light and heavy chain. A single chain Fv ("scFv") polypeptide is a covalently linked VH:VL heterodimer which may be expressed from a nucleic acid including VH- and VL-encoding sequences either joined directly or joined by a peptide-encoding linker. See e.g., Huston, et al. (1988) Proc. Nat. Acad. Sci. USA, 85:5879-5883. A number of structures for converting the naturally aggregated, but chemically separated light and heavy polypeptide chains from an antibody V region into an scFv molecule which will fold into a three dimensional structure substantially similar to the structure of an antigen-binding site.

An alternative to the traditional antibody fragments above has been found in a set of unique antibodies produced by the immune systems of camels, llamas, and sharks. Unlike other antibodies, these affinity reagents are composed of only two heavy chains; better yet, a single domain forms the antigen-binding sites for these heavy-chain antibodies. The domains can even be genetically engineered to produce extremely small, very stable single-domain recombinant antibody fragments, called "nanobodies." Plasmids encoding heavy chain only (VHH), single domain antibodies, and nanobodies are also contemplated for intratumoral delivery by electroporation.

Soluble Antagonists

Antagonists/inhibitors of checkpoint molecules may be soluble binding partners of the checkpoint inhibitors in Table 1, such as soluble PD-L1, which comprises at least the extracellular domain (ECD) of PD-L1. Other soluble checkpoint inhibitors will similarly lack transmembrane and intracellular domains, but are capable of binding to their binding partners and eliciting a biological effect. For intratumoral delivery by electroporation, the ECDs will be encoded in an expression vector and will be expressed when delivered to the tumor.

The soluble encoded form of the checkpoint inhibitor may be linked in the expression vector to DNA encoding another protein or polypeptide. Such other polypeptide may be the Fc portion of an immunoglobulin, albumin, or any other type of serum protein or fragment thereof which maintains the solubility of the checkpoint inhibitor molecule. The soluble form of the checkpoint inhibitor molecule may be linked to an immunoglobulin via the heavy and/or light chain, which may be a fragment or a full length heavy or light chain. The immunoglobulin may be an antibody that can target an antigen associated with a cancer cell or tumor.

The soluble checkpoint inhibitor is delivered either as protein systemically or intratumorally via electroporation, as a nucleic acid. Nucleic add refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids can include RNA, DNA, chimeric DNA-RNA polymers, or analogs thereof. The DNA can be a plasmid expressing a particular soluble checkpoint inhibitor molecule of interest.

The DNA plasmid used for electroporation of encoded soluble checkpoint inhibitor is one that includes an encoding sequence of a recombinant antigen that is capable of being expressed in a mammalian cell upon said DNA plasmid entering after electroporation. Preferably, the encoding sequence is a consensus checkpoint inhibitor molecule that elicits an immune response in the target tumor. In some embodiments, the coding sequence is optimized for mammalian expression, which can include one or more of the following: including the addition of a Kozak sequence, codon optimization, and RNA optimization. These optimized encoding sequences can be subcloned into various commercially available vectors.

Combination Therapies

It is contemplated that systemic delivery of at least one checkpoint inhibitor therapeutic or intratumoral electroporation of plasmid DNA encoding checkpoint inhibitors can be administered with other therapeutic entities, in particular, at least one immunostimulatory cytokine, e.g., intratumoral delivery of IL-12 by electroporation. Administration of the combination therapies can be achieved by electroporation alone or a combination of electroporation and systemic delivery.

Other contemplated combination therapies are checkpoint inhibitors combined with: TLR agonists (e.g., Flagellin, CpG); IL-10 antagonists (e.g., anti-IL-10 or anti-IL-10R antibodies); TGF-β antagonists, CD3 agonists; telomerase antagonists, etc.

With regard to combination therapy utilizing a checkpoint inhibitor and IL-12, clinical studies are ongoing involving systemic administration of pembroluzimab (anti-PD-1 antibody) and intratumoral administration, via electroporation, of DNA encoding an immunostimulatory cytokine, e.g., IL-12. Examples of immunostimulatory cytokines are provided in Table 2. Below is a description of the clinical study and associated data. It is also contemplated that other antagonist PD-1 therapies can be used in combination with intratumoral expression of IL-12. PD-1 antagonists include, one or more of nivolumab (ONO-4538/BMS-936558, MDX1106, OPDIVO, BRISTOL MYERS SQUIBB), pembrolizumab (MK-3475, KEYTRUDA, Merck), pidilizumab (CT-011, CURE TECH), MPDL328OA (ROCHE), etc. These therapies can be administered systemically at recommended dosage levels, or encoded on an expression vector or plasmid and delivered intratumorally by electroporation with the expression plasmid or vector encoding IL-12. It is also contemplated that the genes encoding IL-12 and the PD-1 antagonists are encoded on the same expression vector.

Electroporation

The devices are contemplated for use in patients afflicted with cancer or other non-cancerous (benign) growths. These growths may manifest themselves as any of a lesion, polyp, neoplasm (e.g. papillary urothelial neoplasm), papilloma, malignancy, tumor (e.g. Klatskin tumor, hilar tumor, noninvasive papillary urothelial tumor, germ cell tumor, Ewing's tumor, Askin's tumor, primitive neuroectodermal tumor, Leydig cell tumor, Wilms' tumor, Sertoli cell tumor), sarcoma, carcinoma (e.g. squamous cell carcinoma, cloacogenic carcinoma, adenocarcinoma, adenosquamous carcinoma, cholangiocarcinoma, hepatocellular carcinoma, invasive papillary urothelial carcinoma, flat urothelial carcinoma), lump, or any other type of cancerous or non-cancerous growth. Tumors treated with the devices and methods of the present embodiment may be any of noninvasive, invasive, superficial, papillary, flat, metastatic, localized, unicentric, multicentric, low grade, and high grade.

The devices are contemplated for use in numerous types of malignant tumors (i.e. cancer) and benign tumors. For example, the devices and methods described herein are contemplated for use in adrenal cortical cancer, anal cancer, bile duct cancer (e.g. periphilar cancer, distal bile duct cancer, intrahepatic bile duct cancer) bladder cancer, benign and cancerous bone cancer (e.g. osteoma, osteoid osteoma, osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adenocarcinoma, clear cell) esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer, both melanoma and non-melanoma skin caner), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

The devices and methods of the present embodiment work to treat cancerous tumors by delivering electrical therapy continuously and/or in pulses for a period of time ranging from a fraction of a second to several days, weeks, and/or months to tumors. In a preferred embodiment, electrical therapy is direct current electrical therapy.

The term "electroporation" (i.e, rendering cellular membranes permeable) as used herein may be caused by any amount of coulombs, voltage, and/or current delivered to a patient in any period of time sufficient to open holes in cellular membranes (e.g. to allow diffusion of molecules such as pharmaceuticals, solutions, genes, and other agents into a viable cell).

Delivering electrical therapy to tissue causes a series of biological and electrochemical reactions. At a high enough voltage, cellular structures and cellular metabolism are severely disturbed by the application of electrical therapy. Although both cancerous and non-cancerous cells are destroyed at certain levels of electrical therapy tumor cells are more sensitive to changes in their microenvironment than are non-cancerous cells. Distributions of macroelements and microelements are changed as a result of electrical therapy.

In a single electrode configuration, voltage may be applied for fractions of seconds to hours between a lead electrode and the generator housing, to begin destruction of cancerous tissue. Application of a given voltage may be in a series of pulses, with each pulse lasting fractions of a second to several minutes. In certain embodiments, the pulse duration or width can be from about. Low voltage may also be applied for of a duration of fractions of seconds to minutes, which may attract white blood cells to the tumor site. In this way, the cell mediated immune system may remove dead tumor cells and may develop antibodies against tumor cells. Furthermore, the stimulated immune system may attack borderline tumor cells and metastases.

Various adjuvants may be used to increase any immunological response, depending on the host species, including but not limited to Freund's adjuvant (complete and incomplete), mineral salts such as aluminum hydroxide or aluminum phosphate, various cytokines, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof.

U.S. Pat. No. 7,245,963 by Draghia-Akli, et al. describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk (see, e.g., U.S. Patent Pub. 2005/0052630) is hereby incorporated by reference.

The electrode arrays and methods described in U.S. Pat. No. 7,245,963 and U.S. Patent Pub. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes.

Uptake of the non-viral delivery vectors of the present invention may also be enhanced by plasma electroporation also termed avalanche transfection. Briefly, microsecond discharges create cavitation microbubbles at electrode surface. The mechanical force created by the collapsing microbubbles combined with the magnetic field serve to increase transport efficiency across the cell membrane as compared with the diffusion mediated transport associated with conventional electroporation. The technique of plasma electroporation is described in Vankov, et al. U.S. Pat. No. 7,923,251 issued Apr. 12, 2011 and Vankov, et al U.S. Pat. No. 8,283,171 issued Oct. 9, 2012. This technique may also be employed in vivo for the transformation of cells. Chalberg, et al (2006) Investigative Ophthalmology & Visual Science 47:4083-4090; Chalberg, et al U.S. Pat. No. 8,101,169 Issued Jan. 24, 2012.

Staging of Melanoma Lesions

The TNM system (see, e.g., Edge S B et al. (2010) "Melanoma of the skin", *AJCC Cancer Staging Manual*. 7th ed. New York, N.Y. Springer-Verlag) is used to assess the characteristics of lesions and determine the stage of the disease.

The T (tumor) categories are based on the thickness of the melanoma and other key factors seen in the skin biopsy (tumor thickness, mitotic rate and ulceration). Table 3 provides further categorization of the T group assessments.

TABLE 3

T Classification for primary tumors

| | |
|---|---|
| TX | Primary tumor cannot be assessed (i.e., curettaged or severely regressed melanoma) |

TABLE 3-continued

T Classification for primary tumors

| | |
|---|---|
| T0 | No evidence of primary tumor |
| Tis | Melanoma in situ |
| T1 | Melanoma ≤1.0 mm in thickness |
| | T1a: Without ulceration and mitoses <1/mm² |
| | T1b: With ulceration or mitoses ≥1/mm² |
| T2 | Melanomas 1.01-2.0 mm in thickness |
| | T2a: Without ulceration |
| | T2b: With ulceration |
| T3 | Melanomas 2.01-4.0 mm in thickness |
| | T3a: Without ulceration |
| | T3b: With ulceration |
| T4 | Melanomas >4.0 mm in thickness |
| | T4a: Without ulceration |
| | T4b: With ulceration |

The N (lymph node) categories depend on presence/number of sentinel/distant lymph node(s) with detectable tumor. The M (metastasis) categories depend on presence, location and severity of metastasis. Table 4 provides further categorization of the N group assessments.

TABLE 4

N Classification in regional lymph nodes

| | |
|---|---|
| NX | Patients in whom the regional nodes cannot be assessed (ie, previously removed for another reason) |
| N0 | No regional metastases detected |
| N1-3 | Regional metastases based upon number of metastatic nodes and presence or absence of intralymphatic metastases (in transit or satellite metastases) |
| N1 | 1 lymph node |
| | N1a: Micrometastases |
| | N1b: Macrometastases |
| N2 | 2 or 3 lymph nodes |
| | N2a: Micrometastases |
| | N2b: Macrometastases |
| | N2c: In-transit met(s)/satellite(s) without metastatic lymph nodes |
| N3 | ≥4 metastatic lymph nodes, or matted lymph nodes, or in-transit met(s)/satellite(s) with metastatic lymph node(s) |

Once the T, N, and M groups have been determined, they are combined to give an overall stage, using Roman numerals I to IV (1 to 4) and sometimes subdivided using capital letters. Table 5 provides further categorization of the M group assessments.

TABLE 5

M classifications of metastasis

| | |
|---|---|
| M0 | No detectable evidence of distant metastases |
| M1a | Metastases to skin, subcutaneous, or distant lymph nodes, normal serum lactate dehydrogenase (LDH) level |
| M1b | Lung metastases, normal LDH level |
| M1c | Metastases to all other visceral sites or distant metastases to any site combined with an elevated serum LDH level |

Example of Stage IIIB—T1a to T4a, N2c, M0: tumor can be any thickness, but it is not ulcerated. It has spread to small areas of nearby skin (satellite tumors) or lymphatic channels (in-transit tumors) around the original tumor, but the nodes do not contain melanoma. There is no distant spread.

Example of Stage IV—Any T, any N, M1(a, b, or c): The melanoma has spread beyond the original area of skin and nearby lymph nodes to other organs such as the lung, liver, or brain, or to distant areas of the skin, subcutaneous tissue, or distant lymph nodes.

Measuring Clinical Outcomes

Clinical outcomes in Melanoma trials may be measured by the Response Evaluation Criteria In Solid Tumors (RECIST) criteria. RECIST provides guidelines that define when tumors improve ("respond"), stay the same ("stabilize"), or worsen ("progress").

A sum of the longest diameter (LD) for all target lesions will be the baseline sum LD. This will be used as reference by which to characterize the objective tumor response in the targeted lesion(s).

a. Complete Response (CR) is the disappearance of all target lesions;
b. Partial Response (PR) shows at least a 30% decrease in the sum of the LD of target lesions;
c. Stable Disease (SD) occurs if there no sufficient shrinkage to qualify for PR nor sufficient increase to qualify for Progressive Disease (PD); and
d. Progressive Disease (PD): At least a 20% increase in the sum of the LD of target lesions or the appearance of one or more new lesions.

A "modified" RECIST can also be used to measure outcomes of clinical treatment. Modified "skin" RECIST: calculated by the sum of all measurable (>0.3 cm) lesions. The following criteria will be used to define a measurable tumor lesion: No maximum number of skin lesions will be defined; all measurable skin lesions will be included in the objective tumor evaluation; sum of the all measurable skin lesions used to characterize the response to therapy; and new lesions on skin permitted if sum total increase is <30% from nadir.

An additional more refined measurement, known as Modified Immune-Related Response Criteria (irRC) can be used and may be calculated by the sum of all measurable (>0.3 cm) lesions. The following criteria can used to define a measurable tumor lesion: Up to 10 visceral lesions are permitted as index lesions for evaluation; new lesions do not automatically preclude a complete response (CR); new lesions are added to the sum of diameters once they are considered measurable; and Modified irRC Tumor Burden=$SPD_{Index}+SPD_{New\ measurable}$. SPD is the Sum of Perpendicular Diameters of each lesion. Index represents 10 visceral lesions that are observed prior to treatment, and New measurable represents new lesions that appear during treatment.

Complete response (CR) for both modified "skin" RECIST and modified irRC is defined as complete disappearance of all lesions (whether measurable or not) and the absence of new lesions for at least 4 weeks duration, confirmed by additional scan and visit 4 to 6 weeks after first documentation of CR.

Partial response (PR) is defined as Modified "skin" RECIST: ≥30% decrease in LD from baseline. The date of response is the date of the initial documentation of response. Modified irRC: ≥50% decrease in the product of the diameters from baseline. The date of response is the date of the initial documentation of response.

Progression of disease (PD) is defined as Modified "skin" RECIST: ≥20% increase in the LD. In addition to the relative increase of 20%, the sum must also demonstrate an absolute increase of ≥5 mm2. Modified irRC: ≥25% increase in the products of the diameters.

EXAMPLES

I. Llama Immunization

Antibodies were raised in llamas (Abcore) following a prime/boost method in which the initial three immunizations were given by electroporation of a plasmid encoding the antigen of interest followed by two subsequent protein boosts. Priming by DNA immunization was done on days 1, 14, and 28 by injecting 250 ug of plasmid expressing the extracellular domain of human CTLA-4 intradermally into the llama followed by electroporation and repeating the process in an adjacent area. The llama was then given the last two boosts on days 56 and 84 by subcutaneous injection of 50 ug human CTLA-4 protein (Sino Biological) emulsified with 2 mL of Incomplete Freund's Adjuvant (MP Biologicals). Test bleeds were taken during the duration of the immunization process to monitor titer levels.

II. cDNA Synthesis for The Isolation of Single Domain Antibodies

Peripheral blood lymphocytes (PBL) are isolated from whole blood taken from the llama at the end of the immunization cycle by density gradient separation. Whole blood is mixed 50:50 with PBS supplemented with 2% FBS before centrifugation with Lymphoprep (Stemcell), a density gradient medium. The layer of PBL is isolated and total RNA is extracted from the PBL using an RNeasy maxi kit (Qiagen). cDNA is synthesized using a First-Strand cDNA Synthesis Kit (GE Healthcare).

III. Isolation of Single Domain Antibodies

A nested PCR strategy is used to isolate the VHH genes using the cDNA synthesized from the RNA extracted from PBL of the immunized llama. A primary PCR is performed using forward primers MJ1, MJ2, MJ3, VHBACKA6 and reverse primer CH2FORTA4 (see, e.g., Baral et al., (2013) *Curr. Protoc. Immunol.* 103:2.17.1-2.17.57 and Sabir et al., (2014) *C. R. Biol.*, 337: 244-249) to amplify the variable domains of both VHH and VH. The VHH fragment (~550-650 bp) is separated from the VH fragment (~900 bp) by gel electrophoresis and the VHH fragment is purified using a gel extraction kit (Qiagen). A secondary PCR reaction was done using forward primers MJ7, VHBACKA5 and reverse primers MJ8, F4rev with SfiI restriction sites specific to the pADL-20c (Antibody Design Labs) phagemid vector appended to the flanks. Final PCR products are ligated into the phagemid pADL-20c vector using the SfiI restriction sites. The ligated plasmid is then used to transform electrocompetent TG1 *E. coli* cells for phage display.

The repertoire of VHH is expressed on phage particles after rescuing with M13K07 helper phage (Antibody Design Labs). VHH that is specific to human CTLA-4 is enriched by performing three to five rounds of biopanning against human CTLA-4 recombinant protein coated on Maxisorb microtiter plates (Sigma-Aldrich). Bound phage is eluted by the addition 0.1 M triethylamine. The solution is neutralized by 1 M Tris-HCL at pH 7.4.

Eluted phage is used to infect exponentially growing TG1 cells. Individual clones selected on the last round of biopanning are sequenced and tested against human CTLA-4 in a phage binding ELISA. Clones are grown in 2×YT media supplemented with 0.1 µg/ml carbenicillin and 0.2% glucose to OD~0.5. M13K07 helper phage is then added at a 20-fold excess along with kanamycin at a final concentration of 50 µg/ml. The clones are amplified by incubating overnight at 37° C. with shaking. The clone cultures are then centrifuged at 4000 rpm at 4° C. for 15 minutes to pellet the cells. 100 µl of supernatant containing the phage is transferred to microtiter plates pre-coated with human CTLA-4. After a 2 hour incubation at 37° C., the microtiter plate is washed with 0.1% Tween-20 in PBS (PBST) three times followed by the addition of anti-M13 HRP antibody (Abcam). VHH phages bound to human CTLA-4 is detected by the addition of TMB (Pierce). The development is stopped by the addition of 4N $H_2SO_4$ and the absorption is read on a Spectramax (Molecular Devices) set to OD 450 nm.

IV. CTLA-4 Binding

Interaction with CTLA-4 is measured by the detection of anti-human CTLA-4 antibody or antibody fragment binding to immobilized human CTLA-4 recombinant protein (Sino Biological). Recombinant human CTLA-4 protein is coated on high binding EIA plates (Corning) overnight at 4° C. Following washing of wells with PBST (0.1% Tween-20 in PBS), the plate is blocked with Super Block (Scytek) for 1 hour at room temperature. The plate is washed with PBST and test samples of anti-human CTLA-4 is added to wells and incubated for 1 hour. Wells are washed again with PBST and the secondary goat anti-human IgG (H+L) (Jackson Immunoresearch) is added. After 1 hour of incubation, the secondary is washed off with PBST and the plate is developed with TMB (Pierce). Color development is stopped with 4N $H_2SO_4$ and optical density is read on a spectrophotometer set to 450 nm to measure binding affinity of the anti-human CTLA-4 to human CTLA-4 recombinant protein.

V. B7 and CTLA-4 Competitive Assay

In vitro, anti-human CTLA-4 activity is measured by its ability to block the interaction between human CTLA-4 protein with its ligands, B7.1 and B7.2. Recombinant human B7.1 or human B7.2 (R&D Systems) is coated on high binding EIA plates (Corning) overnight at 4° C. Following washing of wells with PBST (0.1% Tween-20 in PBS), the plate is blocked with Super Block (Scytek) for 1 hour at room temperature. A titration of anti-human CTLA-4 is mixed with a constant concentration of recombinant human anti-CTLA-4. After Super Block is removed from wells and the plate is washed with PBST, the anti-human CTLA-4/human CTLA-4 mixture is added to wells and incubated for 1 hour at room temperature. Wells are washed with PBST and biotinylated anti-human CTLA-4 (R&D Systems) is added to sample wells and incubated for 1 hour. The plate is washed again with PBST and streptavidin-HRP (Abcam) is added to wells. After a 1 hour incubation, unbound streptavidin-HRP is washed off with PBST and the plate is developed with TMB (Pierce). Color development is stopped by addition of 4N $H_2SO_4$ and optical density is read on a spectrophotometer set to 450 nm to measure blocking of human CTLA-4 binding to hB7.1 or hB7.2 by the anti-human CTLA-4 test samples. The inhibition curve is plotted and the $IC_{50}$ is calculated using software such as Prism (Graphpad).

Figure 3:
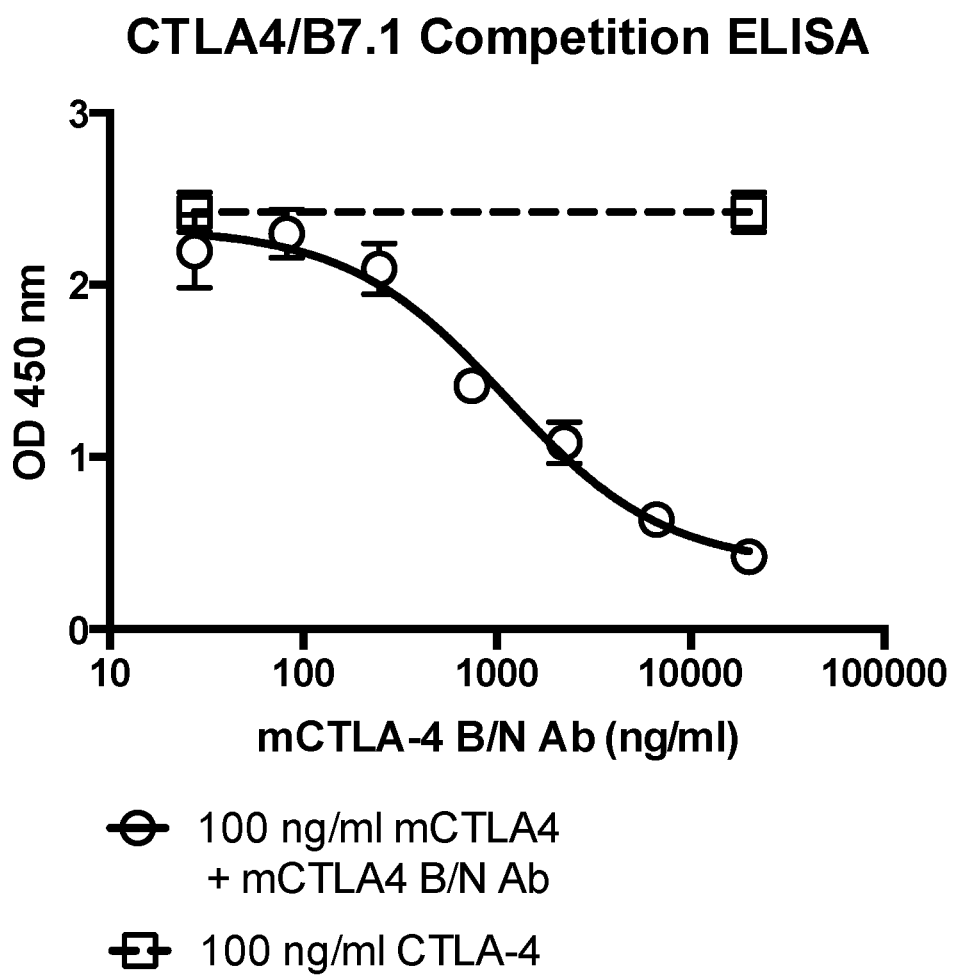
FIG. 3 shows CTLA-4/B7.1 competition ELISA. Anti-mouse CTLA-4 antibodies were used in lieu of anti-human CTLA-4 antibodies.

The above assay was run with anti-mouse CTLA-4 antibody (eBioscience) and 100 ng/ml mCTLA protein (Sino Biological). Results are depicted in FIG. 3.

VI. Jurkat IL-2 Release Assay

Anti-human CTLA-4 activity is measured in a cell system by its ability to block CTLA-4's inhibition of B7-induced IL-2 secretion in Jurkat cells. Jurkat cells (ATCC) are cultured in RPMI-1640 (Corning) supplemented with 10% FBS and 2 mM L-glutamine. Cells are harvested and brought up in assay medium (RPMI-1640 supplemented with 5% FBS and 2 mM L-glutamine) and seeded into wells of a 96-well tissue culture treated plate (Greiner Bio-One). Jurkats are then co-stimulated with PHA-L (Sigma) and recombinant human B7.1 protein (R&D Systems). A constant concentration of recombinant human CTLA-4 protein (R&D Systems) is mixed with a titration of anti-human CTLA-4 and the solution is then added to the stimulated Jurkat cells and incubated in a 37° C., 5% CO2 humidified incubator for 2-3 days. The supernatant is harvested and IL-2 levels is measured using an IL-2 duoset detection kit (R&D systems). Measured IL-2 is graphed and the $EC_{50}$ of the anti-human CTLA-4 is calculated in Prism.

Figure 4:
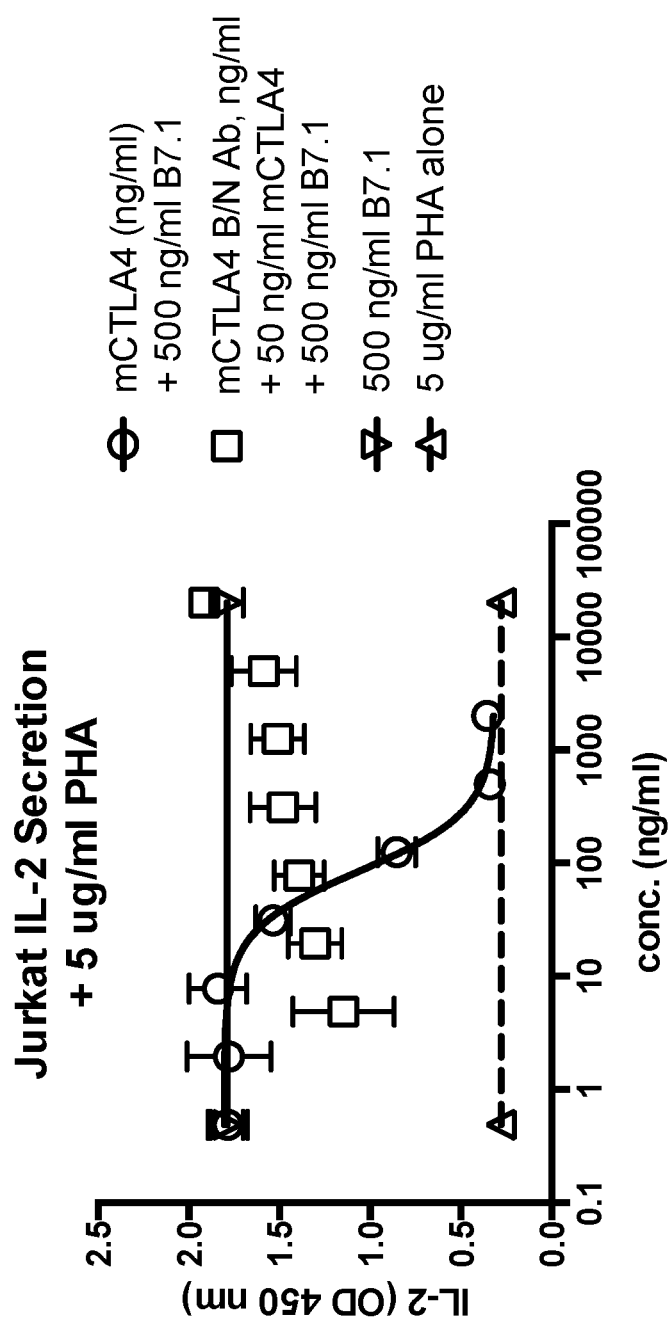
FIG. 4 shows Jurkat cell IL-2 secretion assay data. Mouse CTLA-4 and anti-mouse CTLA-4 antagonist antibodies were used in lieu of the human counterparts. Anti-mCTLA-4 antagonist antibody treatment shows increased production of IL-2.

The above assay was run with the mouse CTLA-4 antibody and protein. Results are depicted in FIG. 4.

VIII. Tumors and Mice

B16.F10 murine melanoma cells (CRL 6475; American Type Culture Collection, Rockville, Md.) are maintained in Dulbecco's minimal Eagle's medium (DMEM) supplemented with 10% FCS and 0.2% gentamicin. Cells are trypsinized and washed in sterile PBS before injection. The left flank of C57BL/6 mice (National Cancer Institute, Bethesda, Md.) is shaved and $1 \times 10^6$ cells in 50 ml of sterile PBS are injected subcutaneously. When challenged, mice ware injected with $5 \times 10^5$ B16.F10 cells in the right flank. Tumors are measured using digital calipers, and treatment is begun when tumors reach 3-5 mm in diameter, 7-10 days after injection. Mice are housed in accordance with AALAC guidelines.

IX. Plasmid DNA pUMVC3 plasmids (ALDEVERON) containing DNA encoding checkpoint inhibitors (e.g., antagonist antibodies or fragments thereof) and IL-12 are generated. pUMVC3 containing a checkpoint inhibitor is prepared with an endotoxin-free kit. All plasmid DNA is diluted in sterile injectable saline (0.9%) and stored at −20° C.

X. Intratumoral Treatment

Mice are anesthetized using 97% oxygen and 3% isoflurane. Tumors are injected with 50 μL (1.0 μg/ml) plasmid DNA in sterile saline using a tuberculin syringe with a 25-gauge needle. An applicator containing six penetrating electrodes 1 cm in diameter is inserted into the tumor. Up to six pulses are delivered at 1500 V/cm (99 its, 1 Hz) using an appropriate pulse generator.

XI. Histology

Mice are humanely sacrificed by $CO_2$ asphyxiation. Tumors are excised and placed in 50-ml conical tubes containing 10 ml of 10% formalin. The tissue is stained with H&E after fixation, as follows: after fixation in 10% neutral buffered formalin for 6 hours, representative tissue samples are processed into paraffin blocks using a Miles VIP tissue processor (Miles Inc., Mishawaka, Ind.). Briefly, tissues are dehydrated in ascending grades of ethanol, cleared in xylene, and infiltrated in paraffin (Tissue Prep 2; Fisher Scientific). Following embedding, tissues are sectioned on a standard rotatory microtome and 4 mm sections are retrieved from a waterbath and mounted on glass slides. Three sections per tumor are examined. Sections are heat-dried and stained with H&E (Richard-Allen Scientific, Kalamazoo, Mich.) using standard histologic techniques.

XII. Immunohistochemistry

Immunohistochemical staining is conducted to examine the tumors for the presence of CD4+ lymphocytes, CD8+ lymphocytes, and blood vessels using the following antibodies: rat anti-mouse CD4, rat anti-mouse CD8 (Ly2), and rat anti-mouse CD31 (PECAM-1), respectively (PharMingen, Cambridge, Mass.). Mice are humanely sacrificed by $CO_2$ asphyxiation. Tumors are excised with scissors and the skin removed, then immediately frozen in a mixture of dry ice and ethanol, and stored at (80° C.). Frozen sections of 5 m are obtained. For immunohistochemical analysis, rat anti-mouse CD4, rat anti-mouse CD8 (Ly2), or rat anti-mouse CD31 (PECAM-1) is applied to tissue sections at a dilution of 1:50 and incubated for 30 minutes, followed by detection with the Vector Elite Rat IgG Peroxidase kit at 2× concentration (15 minutes each in biotinylated anti-rat IgG and ABC complex). Immunostaining is carried out on the Dako autostainer. Sections are analyzed at 400× magnification.

XII. Clinical Study No. 1—Intratumoral IL-12 in Triple Negative Breast Cancer

This study evaluated the pharmacodynamics effects of intratumoral injection of pIL-12 followed immediately by electroporation. Patients were recruited from one study center in the United States. A minimum of ten patients with biopsy-accessible triple negative breast cancer (TNBC) were treated in this study. All patients received a single 28-day treatment cycle. During screening, the investigator selected one control lesion to remain untreated (i.e., non-injected, non-electroporated). The untreated control lesion was at least 0.5 cm in longest diameter and was biopsy accessible. Treatment was administered on Days 1, 5 and 8. A period of ±2 days was allowed for each planned treatment to accommodate scheduling constraints. Treatment was administered to each planned lesion as defined in below. Treatments consisted of intratumoral injection(s) of pIL-12 followed immediately by electroporation. At the end of the treatment cycle, patients returned to clinic for a general safety evaluation and tumor biopsy sampling (End of Study visit). The End of Study (EOS) visit occurred prior to initiating any new anti-cancer therapy/regimen and within 20 days (±2 days) of the last IT-pIL-12-EP treatment.

Patients had histologically confirmed diagnosis of locally-advanced, inoperable, metastatic and/or treatment-refractory triple-negative breast cancer (TNBC). Treatment-refractory disease was defined as the persistence of tumor lesions following at least one prior intervention that may include chemotherapy, radiation and/or surgery, or any combination thereof. Patients must have had both ER and PR staining <5%, and be HER2-negative [immunohistochemistry 0 to 1+ or fluorescence in situ hybridization (FISH) negative]. Patients with ER or PR staining of 5-10%, but who had historically been treated as TNBC may also be enrolled. Patients must NOT have had disease that, in the opinion of the Investigator, was considered amenable to potentially curative treatment. Patients had to have an Eastern Cooperative Oncology Group (ECOG) performance status of 0-1, were ≥18 years of age, and had a Life Expectancy of at least 6 months. Patients may have had radiation therapy, but must have progressive disease after radiation therapy if the lesions to be treated were within the radiation field. In addition, radiation treatment must be completed at least 4 weeks prior to Cycle 1 Day 1. Patients must have had lesions that are accessible for injection and electroporation, defined as cutaneous or subcutaneous disease. Patients must have had at least 2 anatomically distinct lesions accessible for biopsy. One of these lesions remained untreated and evaluated for biomarkers of increased immunogenicity.

DNA plasmid vector (pUMVC3-hIL-12-NGVL331, referred to as "pIL-12"), expressing IL-12 cDNA, contained the human IL-12 p35 and p40 subunits separated by an internal ribosomal entry site driven by a single CMV promoter. pIL-12 was formulated in phosphate buffered saline (PBS) for direct intratumoral injection following in vivo EP. GMP-grade pIL-12 was manufactured by VGXI USA and available batches was supplied as 2.0 mL vials at a concentration of 0.5 mg/mL and fill volume of 1.5 mL. Unopened vials of pIL-12 were stored in a secure, continuously temperature monitored and alarmed freezer in the pharmacy or other appropriate secure location at −20° C.±5° C. If any temperature excursions occurred, then the study sponsor was notified before the pIL-12 plasmid was utilized for study treatment. Receipt and dispensing of trial medication was recorded by an authorized person at the trial site. Clinical supplies were not used for any purpose other than that stated in the protocol.

Prior to plasmid injection, using sterile precautions, 1% lidocaine was injected around the lesion to obtain local anesthesia. Alternative local anesthetics was used as clinically indicated and deemed clinically optimal. In addition, the patient was given analgesics or anxiolytics as necessary prior to or during treatment. If local anesthesia was injected directly into the lesion to mitigate discomfort, a minimum of 2 minutes was allowed to pass for tissue diffusion prior to injecting plasmid. In situations involving patients with extensive disease, conscious sedation was utilized at the discretion of the treating investigator to better manage and minimize patient discomfort. Conscious sedation was performed per institutional guidelines and requirements.

After injecting the plasmid solution into the accessible lesion, a sterile applicator containing 6 stainless steel electrodes arranged in a circle was placed around the tumor. The applicator was connected to the power supply and six pulses at a field strength (E+) of 1500 V/cm and pulse width of 100 µs at 1-second intervals was administered to each previously injected tumor. The electroporation pulses were between six hexagonal opposing needle electrodes. After the first pulse, the polarity between the opposing needle electrode pairs was reversed and the needle pair is pulsed again. After the initial paired pulse, the pulse delivery was rotated clockwise to the next opposing needle pairs until a total of six pulses were delivered to complete the electroporation sequence. Once a lesion has been completely treated, the next tumor was injected and immediately electroporated. Use of ultrasound guidance was recommended for treatment of lesions where additional structural mapping would be appropriate.

Plasmid solution was dispensed at a concentration of 0.5 mg/mL. Tumor size was used to calculate the total dose per lesion and per patient. Unused portions of each vial were discarded into approved biohazard containers and disposed of as per institutional requirements. On dosing days (Days 1, 5 and 8 of the treatment cycle), the site pharmacist, or designated personnel authorized by the Principal Investigator, removed the required number of pIL-12 vials from −20° C. freezer for thawing. Once thawed, the dosing solution was prepared aseptically. Administration of dosing solution to the subject was within 8 hours preparation. For additional details on plasmid storage, handling, and preparation, please refer to the Pharmacy Manual.

At the initial examination, Accessible Lesions (ALs) were determined. ALs to be treated were selected prior to the treatment cycle and measured in centimeters. Plasmid injection volume (P) for each lesion was calculated with the following formula: $P = ab2/8$.

Where (a) is the longest diameter and (b) is the diameter perpendicular to (a) in centimeters. Each lesion received a minimum plasmid injection volume of 0.1 mL. For small lesions with a calculated P volume of less than 0.1 mL, the minimum volume of 0.1 mL was administered. There was no defined maximum number of lesions to be treated, but the total plasmid injection volume per patient per day was not to exceed 20 mL. When appropriate, each treatment syringe was filled with an additional 0.1 mL to the calculated plasmid injection volume to account for needle dead space. Each lesion treated on day 1 of the cycle was also be treated at Days 5 and 8 of that cycle. For larger lesions, plasmid injections and electroporation were directed to the peripheral margins of the tumor, which was thought to represent the most immunologically active aspect of the tumor.

An individual subject was considered to have completed the study if the patient received all three IT-pIL-EP treatments (Day 1, 5, 8), all required pre- and post-treatment tumor biopsies were obtained, and EOS safety follow-up evaluations were performed. Duration of study participation was approximately 4 weeks for each patient. The study was completed once the last patient completed all required treatment and completes the EOS safety follow-up evaluation. The total study duration was expected to be approximately 12 months. Approximately 10 months was required to enroll all subjects.

At screening, the investigator identified accessible lesion(s) for injection and electroporation, defined as cutaneous or subcutaneous disease. An accessible lesion was one that can be reached from the surface with the electroporation needle array. The probes of the needle array reached up to 1.5 cm depth. Only documented accessible lesions that were in a suitable, safe location for application of electroporation were eligible for treatment. The same accessible lesions were treated Days 1, 5, and 8 of the treatment cycle.

At screening, the investigator designated one anatomically distinct lesion as the control lesion, to remain untreated (i.e., non-injected, non-electroporated). This control lesion was biopsy accessible.

All patients consented to study-specific tumor biopsies at each of two separate timepoints (pre-treatment and EOS) for molecular and histological analysis. At least one biopsy sample was required at Screening; additional biopsies were optional and were obtained if feasible. A set of post-treatment biopsy samples of one untreated lesion (control lesion) and at least one treated lesion were obtained at EOS. For patients with evidence of either tumor lesion regression or progression prior to EOS, tumor biopsy samples were requested at the first sign of tumor change. At the discretion of the investigator, a pathology core review team were available to facilitate collection of biopsy samples and to ensure collected samples obtained sufficient amount of tumor for analyses. All biopsy samples obtained were evaluated for the presence of tumor-infiltrating lymphocytes (TILs), IL-12 expression, and other markers of enhanced immunologic or immunogenic phenotype by multi-parametric immunohistochemistry (IHC) and Nanostring®. Additional biomarker evaluations were performed based upon emerging data. Biomarker analyses require the comparison of pre-treatment and post-treatment biopsies that contained an adequate and representative sampling of patients' tumors. In the event a biopsy sample doesn't contain a sufficient amount of tumor, the Sponsor requested the following as appropriate: archival tumor tissue obtained within 90 days prior to Screening AND with no administration of systemic therapy for cancer in the interim if inadequate tumor sampling at Screening/Baseline. Permission from the patient to obtain additional biopsies of treated and/or untreated lesions if inadequate tumor sampling at the EOS visit.

The primary objective of the study was to evaluate the potential of IT-pIL12-EP to promote a pro-inflammatory molecular and histological signature both locally and systemically. This was assessed by comparing the presence of TILs at baseline (i.e., pre-treatment) with post-treatment biopsies.

The paired tumor biopsy samples were (6-plex IHC) method with VECTRA immunohistochemistry platform (Perkin-Elmer). This platform employs spectral deconvolution imaging to separate optical signals from each antibody together with state-of-the-art image analysis capabilities to facilitate robust quantitative slide-based immunophenotyping. Data were generated in the form of total positive cells, positive cells/mm2 or percentage positive cells in a population. Each sample was stained with 3 sets of 6-multiplexed stains using adjacent tissue sections. Quantitative analysis of TIL distribution (i.e. intratumoral, stromal, and interface/invasive margin) was performed.

It is hypothesized that successful transduction of IL-12 will result in a broad gene expression pattern characteristic of immunological activity, including but not restricted to, (1) upregulation of interferon-gamma (IFNγ) and IFNγ-downstream target genes; (2) upregulation of antigen presentation and processing machinery (APM); lineage-specific genes reflecting influx/expansion of TILs, specifically NK cells and CD8 T cells. Comparison of NanoString-based gene expression profiles was completed from the paired tumor samples obtained at screening and subsequent to treatment. NanoString's human immunology panel was used for this analysis, representing approximately 600 probes for mRNA species of immunologic significance, including a subset of specific transcripts reflecting interferon pathway activation, antigen presentation and processing machinery (APM) upregulation and immune cell infiltration. These include, but are not limited to, CD3e, CD8a, PD-1, PD-L1, CTLA-4, IFN-γ, CCR5, IDO-1, CXCL-10, CXCL-11, IRF-1, and CD80. Data was normalized and assessed for the presence or absence of target transcripts. RNA extracted from each sample (approx. 50 ng) was run using the nCounter® GX Human Immunology v2 panel. Data was normalized and assessed for the presence or absence of target transcripts. Change in outcome was evaluated from pre and post treatment samples in paired data.

Based upon the availability of tumor tissue following the primary endpoint analyses, the following evaluations are performed:

Multiparametric Flow Cytometric Analysis

Detailed flow cytometric immunophenotyping of tumor tissue samples to test the hypothesis that IT-pIL12-EP treatment leads to an increase in TILs is performed. TILs are isolated from the pre- and post-treatment tumor samples and stained with 3 immunophenotyping antibody panels (Table 2). Live cells are analyzed using a multi-laser flow cytometer and analyzed using FLOWJO single cell analysis software (FlowJo, LLC).

XII. Clinical Study No. 2—Intratumoral IL-12 Treatment of Melanoma and Post-Treatment with a Checkpoint Inhibitor This phase 2 study assessed safety, antitumor activity, and immunologic effects of intratumoral IL-12 plasmid electroporation in advanced melanoma. Patients received treatment, plasmid injection/electroporation to accessible lesions, on days 1, 5 and 8 of each 90 day treatment cycle. Response was assessed after each treatment cycle. Safety evaluations (clinical examination and laboratory assessments) were conducted for all treated patients prior to initiation of therapy and at regular intervals. The severity of adverse events was graded according to the National Cancer Institute Common Terminology Criteria for Adverse Events, version 4.0.

Eligible patients had pathologically documented metastatic melanoma, stages IIIB/C or IV, with at least one subcutaneous or cutaneous lesion accessible for injection/electroporation. Patients had to have an Eastern Cooperative Oncology Group (ECOG) performance status of no more than 2, have adequate renal, hepatic and bone marrow function (creatinine <2× upper limit of normal, bilirubin within institutional normal limits, absolute neutrophil count >1,000/mm3, and a platelet count >100,000/mm3). Patients with electronic pacemakers were excluded from the study.

The plasmid pUMVC3-hIL-12-NGVL331 was produced under Good Manufacturing Practices (GMP) conditions at VGXI Incorporated (The Woodlands, Tex.) and supplied in sterile vials at a final concentration of 2.1 mg/mL and stored at −80° C. Before use, plasmid was thawed to 4° C. and diluted with sterile saline to the required concentration, 0.5 mg/mL.

Lidocaine was applied around each tumor site, and all patients were offered intravenous analgesic (morphine sulfate) and/or anxiolytic (lorazepam) medications before treatment. Plasmid solution was injected using a 25-gauge needle into the tumor nodule. A sterile applicator containing six needle electrodes arranged in a circle was inserted into the tumor and six pulses at field strength of 1,500 V/cm and pulse duration of 100 μs were applied using the OncoSec Medical Electrotherapy System (OncoSec Medical Inc., San Diego, Calif.). Treatments were performed on days 1, 5, and 8.

Plasmid was dispensed at 0.5 mg/mL. Plasmid injection volume was calculated using the formula P=V/4, where P is the plasmid injection volume and V is the estimated tumor volume. Tumor volume was estimated using the formula V=ab2/2 where a is the longest diameter and b is the next longest diameter perpendicular to a in any dimension. A maximum plasmid injection volume of 1 mL (maximum of 0.5 mg plasmid) was permitted per treatment day, distributed over 1-4 accessible lesions.

Disease evaluation for the primary endpoint for overall response rate was assessed by a modification of Response Evaluation Criteria in Solid Tumors (RECIST) that allowed for measurement of tumor burden for in-transit cutaneous and subcutaneous metastatic melanoma, modified "skin" RECIST. Tumor burden at baseline included lesions measured by clinical exam and CT, with no maximum number of skin lesions to allow for accurate accounting of patients' disease status. New lesions at post-treatment disease evaluations were added to the tumor burden and did not indicate progressive disease (PD). Progressive disease (PD) was defined by a 20% or greater increase in tumor burden, and stable disease (SD) by an increase in tumor burden of less than 20% with a duration of at least 90 days. Partial response (PR) was defined by a 30% or greater decrease in tumor burden, and patients with a complete response (CR) had no evidence of disease with complete radiologic and clinical evaluation.

Overall response rate by a modification of immune-related Response Criteria (irRC) for cutaneous lesions was assessed as a secondary response endpoint. Local and distant regression rates of individual lesions was assessed in injected/electroporated lesions and non-injected/non-electroporated lesions. Time to objective response, time to progression (TTP), duration of response (DOR) and progression free survival (PFS) were assessed in the efficacy evaluable population. Long-Term Follow-Up and Survival.

Patients were followed at regular intervals upon study discontinuation for progression, overall survival, and post-treatment therapies for up to 5 years.

In certain patients, following an interval of no treatment, anti-PD-1 or anti-PD-L1 therapies were administered. Patients were again evaluated for responses as described above. Table 3 summarizes a retrospective analysis of the patients receiving additional checkpoint inhibitor therapy following plasmid IL-12 electroporation.

TABLE 3

Clinical analysis of sequential plasmid IL-12 electroporation checkpoint inhibitor therapy.

| Patient ID Number | Interval (days) between last EP treatment and start of anti-PD-1 therapy | Name of anti-PD-1/PD-L1 Therapy (e.g., Pembrolizumab; Nivolumab; ipilimumab) | Response (CR = Complete Response; PR = Partial Response; SD = Stable Disease; PD = Progressive Disease) | Therapy during Interval |
|---|---|---|---|---|
| 100-001-003 | 188 | Pembrolizumab | CR | NO |
| 100-001-006 | 189 | Pembrolizumab | PD | NO |
| 100-001-012 | 98 | Pembrolizumab | CR | NO |
| 100-001-013 | 121 | Pembrolizumab | CR | NO |
| 100-001-014 | 617 | Pembrolizumab | PR | YES |
| 100-001-015 | 49 | Pembrolizumab | CR | NO |
| 100-001-020 | 112 | Pembrolizumab | SD | NO |
| 100-001-102 | 68 | MED14736, trametinib | PR | NO |
| 100-001-106 | 74 | Pembrolizumab | PR | NO |
| 100-001-109 | 34 | Pembrolizumab | SD | NO |
| 100-001-110 | 34 | Nivolumab, ipilimumab | PD | NO |
| 100-001-111 | 36 | Pembrolizumab | PR | NO |
| 100-001-112 | N/D | Pembrolizumab | PD | NO |
| 100-001-113 | 21 | Pembrolizumab | CR | NO |

In addition to systemic PD-1 inhibitor treatment, patients are concurrently treated with plasmid IL-12 electroporation with a subsequent interval of about 20-120 days, e.g., following the interval, a treatment using a checkpoint inhibitor, e.g., anti-PD-1 or anti-PD-L1, is administered alone or in combination with another cycle (treatment on day 1, 5, and 8) of plasmid IL-12 electroporation.

XIV. Addendum to Clinical Study No. 2

An addendum protocol to the initial phase 2 study described above was initiated to assess similar safety, antitumor activity and immunologic effects of IT-IL12-EP in patients treated on a more frequent treatment regimen. Patients received treatment on days 1, 8 and 15 with subsequent cycles every 6 weeks (Regimen A), or treatment on days 1, 5 and 8 every 6 weeks (Regimen B) for up to 9 treatment cycles in total. Study populations were grouped according to the assigned treatment schedule: Regimen A, Regimen B and Regimen A/B. Patients in Regimen A/B included patients who started the study receiving Regimen A, but whose treatment schedule was changed to Regimen B during study participation. Response was assessed every 12 weeks and safety evaluations were conducted prior to initiation of therapy and at regular intervals.

While the dose of pIL-12 vector and its preparation were the same, the vector used in the amendment was formulated in physiologically compatible buffer, e.g., phosphate buffer, for injection (sWFI) for direct intratumoral injection.

XV. Clinical Study No. 3—Treatment of Melanoma with a Combination of Intratumoral IL-12 Electroporation and Checkpoint Inhibitor This is multi-center, Phase II, open label, single-arm trial of intratumoral pIL-12 EP in combination with pembrolizumab in patients with melanoma. Evaluable patients (n=42) initiate treatment with pembrolizumab after the first cycle of intratumoral pIL-12 EP. Pembrolizumab is administered at 200 mg flat dose every 3 weeks starting at Cycle 2. Cycles of intratumoral pIL-12 EP (each cycle consisting of treatment on days 1, 5 and 8) occurs every 6 weeks as long as patients have accessible lesions for EP. Patients are evaluated for response every 12 weeks. Patients will continue on therapy if they have stable disease or better, defined under investigator evaluation at the time of disease evaluations. Therapy is given until disease progression or unacceptable toxicity. Best overall response rate (BORR), CR+PR, within 24 weeks of first treatment with pIL-12 EP and pembrolizumab are determined using RECIST v1.1 or modified RECIST by investigator evaluation and compared against historical rates for pembrolizumab as a monotherapy in a similar population. Additionally, adverse events defined as safety and tolerability, are assessed using the NCI CTCAE version 4.0. Other endpoints addressed in this trial include duration of response (DOR) for those experiencing CR or PR, 24-week landmark progression free survival (PFS as defined by the duration between the date of treatment initiation to the first date of either disease progression or death at 24), overall survival (OS) and best overall response rate (CR+PR).

Patients with melanoma with progressive locally advanced or metastatic disease that is not amenable to definitive local therapy with curative intent are eligible. Patients are intended to have an untreated lesion when there are 3 or more visible, treatable lesions present. In addition, patients must have histological or cytological diagnosis of melanoma with progressive locally advanced or metastatic disease that is not amenable to definitive local therapy with curative intent and have at least one tumor accessible for intratumoral injection and EP on investigator's assessment. Patients may have had prior chemotherapy or immunotherapy or radiation therapy with all prior therapies stopped 4 weeks prior to first dose of study treatment (ipilimumab must be stopped 6 weeks prior). Patients are prohibited from receiving live vaccines within 30 days prior to first dose of study treatment or using any other form of antineoplastic therapy while on study; including systemic chemotherapy, biological therapy, immunotherapy not specified in this protocol.

The plasmid pUMVC3-hIL-12-NGVL331 was produced under Good Manufacturing Practices (GMP) conditions at VGXI Incorporated (The Woodlands, Tex.) and is formulated in phosphate buffered saline (PBS) for direct intratumoral injection following by in vivo EP. The plasmid will be supplied as 2.0 mL vials at a concentration of 0.5 mg/mL and fill volume of 1.5 mL.

Prior to plasmid injection, using sterile precautions, 1% lidocaine can be injected around the lesion or all lesions intended for IT-pIL-12 EP to obtain local anesthesia. In addition, the patient can be given analgesics or anxiolytics as necessary prior to or during treatment. After injecting the plasmid solution into the accessible tumor, a sterile applicator containing 6 stainless steel electrodes arranged in a circle are placed into or around the tumor. The applicator will be connected to the power supply and six pulses at a field strength (E+) of 1500 V/cm and pulse width of 100 μs at 1-second intervals will be administered to each previously injected tumor. EP following intratumoral pIL-12 injection delivers controlled electrical pulses in a square wave pulse pattern, yielding optimal transmembrane potential for electroporation to occur39. The electroporation pulses are between six hexagonal opposing needle electrodes. After the first pulse, the polarity between the opposing needle electrode pairs is reversed and the needle pair is pulsed again. After the initial paired pulse, the pulse delivery is rotated clockwise to the next opposing needle pairs until a total of six pulses are delivered to complete the electroporation sequence. When multiple tumors are being injected on the same day, EP should be performed immediately after the plasmid injection for each tumor. Once a tumor has been completely treated, the next tumor can be injected with plasmid and immediately electroporated.

All trial treatments are administered on an outpatient basis. Intratumoral pIL-12 is given as a single agent for Cycle one. Thereafter, starting at the odd Cycle 3, intratumoral pIL-12 is given first followed by a minimum of 60 minutes observation period between the two treatments.

Intratumoral pIL-12 followed by EP is administered at each odd cycle as long as the subject had at least one accessible superficial lesion (ASL) for treatment. An ASL is defined as meeting the following criteria; (1) at least 0.3 cm×0.3 cm in longest perpendicular diameters, (2) in a suitable location for application of electroporation. In a case where a subject may have multiple ASLs, the maximum number of lesions should be treated at each cycle, keeping in mind, (1) patient tolerability, and (2) not to exceed the maximum daily dose of 20 mL. Prior to initiation of a new treatment cycle of pIL-12 EP, the Investigator will determine ASLs for treatment during that cycle. The same ASLs should be treated on each day of the cycle (i.e. Days 1, 5, 8). Previously treated, previously identified lesions present at baseline that were left untreated, and new lesions which appear during the course of the study that meet the definition of an ASL may be treated as long as the maximum plasmid injection volume per patient per day does not exceed 20 mL. If no ASLs are present at subsequent cycles, the subject may skip that cycle of pIL-12 and continue on the study calendar. When feasible one lesion should remain untreated during cycle 1 to permit biopsy of an untreated lesion, see section 6.1.2.3).

Pembrolizumab (Merck & Co., NJ) is a potent and highly selective humanized mAb of the IgG4/kappa isotype designed to directly block the interaction between PD-1 and its ligands, PD-L1 and PD-L2. This antibody is supplied in a solution for injection at 100 mg/4 mL with each dose of 200 mg being administered intravenously to the patient. Pembrolizumab should be administered at the start of every cycle (after cycle 1 of IT-PIL-12 only), on Day 1 of cycle (±3 days) after all procedures/assessments have been completed. Pembrolizumab is administered as a 30 minute IV infusion (treatment cycle intervals may be increased due to toxicity as described in Section 5.2).

Response and progression in this study is evaluated using the new international criteria proposed by the Response Evaluation Criteria in Solid Tumors (RECIST) Committee [JNCI 92(3):205-216, 2000]. Changes in only the largest diameter (unidimensional measurement) of the tumor lesions are used in the RECIST v1.1 or modified RECIST criteria.

Measurable Disease:

Neoplastic masses that can be precisely measured in 2 in-plane perpendicular diameters. Both its longest diameter and its longest perpendicular must be greater than or equal to 10 mm or 2 times the axial slice thickness. Lymph nodes must have a short-axis line-length of 15 mm. Malignant lymph nodes must be measurable in 2 perpendicular diameters. Both its longest diameter and its longest perpendicular must be greater than or equal to 15 mm or 2 times the axial slice thickness. The quantitative endpoint will be defined as the product of the longest diameter with its longest perpendicular.

Non-Measurable Disease:

Non-measurable lesions are those that are not suitable for quantitative assessment over time. These include:

1. Neoplastic masses that are too small to measure, because their longest uninterrupted diameter or longest perpendicular are less than 10 mm or two times the axial slice thickness.

2. Neoplastic masses whose boundaries cannot be distinguished. This includes masses which cannot be demarcated from surrounding tissue because of inadequate contrast, masses with overly complex morphology, or those with highly heterogeneous tissue composition.

3. Other types of lesions that are confidently felt to represent neoplastic tissue, but difficult to quantify in a reproducible manner. These include bone metastases, leptomeningeal metastases, malignant ascites, pleural/pericardial effusions, inflammatory breast disease, lymphangitis cutis/pulmonis, cystic lesions, ill defined abdominal masses, etc.

Additionally, a modified immune related-Response Criteria (irRC) for the current protocol is adopted from Wolchok et al (2009) and can be used in the evaluation of the secondary objectives. For irRC, only target lesions selected at baseline and measurable new lesions are taken into account.

Upon completion of Safety Follow-up, all patients enter the Survival Follow-up Phase unless they withdraw consent for further data collection or the safety requirements are met. Radiologic monitoring continues (1) until start of a new anti-cancer treatment, (2) until documented disease progression, or (3) until death, whichever occurs first. Radiographic imaging in follow-up may be performed as clinically indicated or per local standard of care. Long term follow up inquiries can include the following:

Date of first progression (if the first progression has not occurred prior to entry in the Follow-Up Phase)

Follow-up therapy for the treatment of melanoma (including radiation, anticancer treatment, adjuvant therapies or surgeries)

Resolution of AEs and SAEs ongoing at the time of entry into survival follow-up

Status (alive, no evidence of disease, alive with disease, deceased)

Cause and date of death (if applicable)

What is claimed is:

1. A method of treating a subject having a treatment-refractory, cutaneous or subcutaneous, cancerous tumor, the method comprising:
    a) injecting the treatment-refractory cutaneous or subcutaneous cancerous tumor with an effective dose of at least one plasmid coding for at least one immunostimulatory cytokine;
    b) administering electroporation therapy to the tumor; and
    c) administering an effective dose of an immune checkpoint inhibitor to the subject.

2. The method of claim 1, wherein the electroporation therapy comprises the administration of at least one voltage pulse over a duration of about 100 microseconds to about 1 millisecond.

3. The method of claim 2, wherein at least one voltage pulse delivered to the tumor has a field strength of about 200 V/cm to about 1500 V/cm.

4. The method of claim 1, wherein the immune checkpoint inhibitor is a PD-1 or PD-L1 antagonist.

5. The method of claim 4, wherein the PD-1 or PD-L1 antagonist is encoded on the plasmid encoding the immunostimulatory cytokine or on a second plasmid and delivered to the cancerous tumor by electroporation therapy.

6. The method of claim 4, wherein the PD-1 or PD-L1 antagonist is administered systemically.

7. The method of claim 6, wherein the PD-1 or PD-L1 antagonist is selected from the group consisting of: nivolumab, pembrolizumab, pidilizumab, and MPDL3280A.

8. The method of claim 4, wherein the PD-1 or PD-L1 antagonist is administered after electroporation of the tumor.

9. The method of claim 1, wherein the plasmid encoding for the at least one immunostimulatory cytokine comprises a nucleic acid encoding an IL-12 p35 subunit and an IL-12 p40 subunit.

10. The method of claim 1, wherein the treatment-refractory cutaneous or subcutaneous cancerous tumor is a treatment-refractory, cutaneous or subcutaneous, breast cancer tumor or a treatment-refractory, cutaneous or subcutaneous, triple-negative breast cancer tumor.

11. The method of claim 1, wherein the cancerous tumor is melanoma.

12. A method of treating a subject having a treatment-refractory, cutaneous or subcutaneous, cancerous tumor comprising:
   a) administering a first treatment at a first time (T1), wherein the first treatment comprises injecting the cancerous tumor with a first effective dose of at least one plasmid encoding at least one immunostimulatory cytokine and administering a first electroporation therapy to the cancerous tumor, wherein the first electroporation therapy further comprises administration of at least one voltage pulse having a duration of about 100 microseconds to about 1 millisecond;
   b) administering a second treatment at a second time (T2) after T1, wherein the second treatment comprises injecting the cancerous tumor with a second effective dose of at least one plasmid encoding at least one immunostimulatory cytokine and administering a second electroporation therapy to the cancerous tumor, wherein the second electroporation therapy further comprises administration of at least one voltage pulse having a duration of about 100 microseconds to about 1 millisecond;
   c) administering a third treatment at a third time (T3) after T2, wherein the third treatment comprises injecting the cancerous tumor with a third effective dose of at least one plasmid encoding at least one immunostimulatory cytokine and administering a third electroporation therapy to the cancerous tumor, wherein the third electroporation therapy further comprises administration of at least one voltage pulse having a duration of about 100 microseconds to about 1 millisecond; and
   d) administering a fourth treatment at a fourth time (T4) after T3, wherein the fourth treatment comprises administering an effective dose of an immune checkpoint inhibitor to the subject.

13. The method of claim 12, wherein:
   a) T1 is day 1;
   b) T2 is day 5;
   c) T3 is day 8; and
   d) T4 is day 20-120.

14. The method of claim 12, wherein the method further comprises:
   a) at least one cycle of intratumoral delivery of the at least one plasmid encoding for the at least one immunostimulatory cytokine by electroporation;
   b) an interval of at least 20-120 days following the one cycle; and
   c) administration to the subject, the immune checkpoint inhibitor or a combination of at least one immune checkpoint inhibitor with at least one additional cycle of intratumoral electroporation therapy.

15. The method of claim 1, wherein said at least one plasmid coding for the at least one immunostimulatory cytokine is a plasmid encoding an IL-12 p35 subunit and an IL-12 p40 subunit separated by an internal ribosomal entry site.

16. The method of claim 4, wherein the PD-1 or PD-L1 antagonist is an anti-PD-1 or anti-PD-L1 antibody.

17. The method of claim 1, wherein said at least one plasmid coding for the at least one immunostimulatory cytokine is a plasmid encoding an IL-12.

18. The method of claim 12, wherein the treatment-refractory, cutaneous or subcutaneous, cancerous tumor is a treatment-refractory, cutaneous or subcutaneous, melanoma tumor or lesion.

* * * * *

UNITED STATES PATENT AND TRADEMARK OFFICE
CERTIFICATE OF CORRECTION

PATENT NO. : 10,426,847 B2
APPLICATION NO. : 15/561915
DATED : October 1, 2019
INVENTOR(S) : Robert H. Pierce and Adil Daud Page 1 of 1

It is certified that error appears in the above-identified patent and that said Letters Patent is hereby corrected as shown below:

On the Title Page

At Item (71), Applicants:
"Robert H. Pierce, Seattle, WA (US); Adil Daud, Hillsborough, CA (US)"

Should read:
-- OncoSec Medical Incorporated, San Diego, CA (US) --

Signed and Sealed this
Twenty-fifth Day of February, 2020

Andrei Iancu
*Director of the United States Patent and Trademark Office*